United States Patent [19]

Wang

[11] Patent Number: 5,604,302

[45] Date of Patent: Feb. 18, 1997

[54] STARCH GELATINIZATION MEASURING SYSTEM

[76] Inventor: Wei-Chi Wang, 2F, No. 3, Alley 24, Lane 92, Sec. 2, Kingsun S. Road, Taipei, Taiwan

[21] Appl. No.: 641,420

[22] Filed: May 1, 1996

[51] Int. Cl.$^6$ .................................................. G01N 37/00
[52] U.S. Cl. ......................... 73/64.41; 324/693; 205/335
[58] Field of Search ........................... 73/64.41; 324/693, 324/71.1; 204/DIG. 7; 205/334, 335, 336, 337, 338, 339

[56] References Cited

U.S. PATENT DOCUMENTS

| 731,339 | 6/1903 | Chapman | 392/314 |
|---|---|---|---|
| 3,560,354 | 10/1967 | Young | 205/338 |
| 5,084,153 | 1/1992 | Mosse et al. | 204/228 |
| 5,360,625 | 11/1994 | Sikking et al. | 426/573 |
| 5,440,667 | 8/1995 | Simpson et al. | 392/314 |

*Primary Examiner*—Robert Raevis
*Assistant Examiner*—Jay L. Politzer
*Attorney, Agent, or Firm*—Bacon & Thomas

[57] ABSTRACT

A starch gelatinization measuring system including an ohmic heater to hold and to heat the starch sample to be measured, the ohmic heater having a pair of plate electrodes for heating; a power supply unit electrically connected to the ohmic heater to control the supply of electric current and electric voltage to the plate electrodes of the ohmic heater; a temperature detector controlled to detect the temperature of the starch sample being heated by the ohmic heater; a data logger electrically connected to the power supply unit and the temperature detector to record the data of temperature, electric current, electric voltage during heating; and a computer electrically connected to the data logger to analyze the data provided by the data logger.

5 Claims, 3 Drawing Sheets

STARCH GELATINIZATION MEASURING SYSTEM

BACKGROUND OF THE INVENTION

The present invention relates to a measuring system and more particularly relates to a measuring system for measuring the degree of starch gelatinization.

When starch is heated with water, starch granules will swell with water, and change from a suspension state into a semi-transparent gelatinous condition. This process is industrially called starch gelatinization. The degree of starch gelatinization has great concern with the quality of the product, will cause certain physical properties changes of the product. For example, viscosity will indirectly affect parameter control during the processing of the product.

DSC (differential scanning calorimetry) is one of the most popularly used methods for measuring the degree of starch gelatinization. However, DSC has some drawbacks as outlined hereinafter. 1. DSC cannot be performed on the production line, and a procedure of sampling is needed before the measurement. 2. Selected sample must be sealed in an aluminum case and heated during the measurement; the temperature detector can only detect the temperature of the aluminum case instead of the temperature of the sample. 3. The hardware instrument is expensive, and only well-trained persons can operate the instrument. 4. Precipitation of starch will happen during the measurement, which may cause errors of measurement. 5. A complicated calibration procedure and a low scanning speed (about 5–10° C./min) must be employed during the measurement, and the result of measurement cannot be known within one hour after the beginning of measurement.

SUMMARY OF THE INVENTION

The present invention has been accomplished to provide a starch gelatinization measuring system which eliminates the aforesaid drawbacks. It is one object of the present invention to provide a starch gelatinization measuring system for measuring the degree of starch gelatinization in an economic and precise way.

It is another object of the present invention to provide a starch gelatinization measuring system which greatly reduces the measuring time.

It is still another object of the present invention to provide a starch gelatinization measuring system which is practical for measuring the degree of starch gelatinization of chemical products and foodstuffs.

It is still another object of the present invention to provide a starch gelatinization measuring system which measures the degree of starch gelatinization by measuring the electrical conductivity of starches when gelatinization occurs, and using the curve-integration calculation.

According to the preferred embodiment of the present invention, the starch gelatinization measuring system comprises an ohmic heater, a shaker, a power supply unit, a temperature detector, a data logger, and a computer. The starch sample ready for test is put in the ohmic heater. The ohmic heater has a pair of plate electrodes for heating. Because starch is not soluble, the solution is a suspension. The ohmic heater can be mounted on the shaker and shaken to keep well mix of the starch sample during the test. The power supply unit is electrically connected to the ohmic heater as the electricity resource. The temperature detector detects the temperature of the starch sample when the starch sample is heated. The data of temperature, current and voltage are recorded by the data logger and transferred to the computer during the test, and analyzed by the computer.

DETAILED DESCRIPTION OF THE PREFERRED EMBODIMENT

Figure 1:
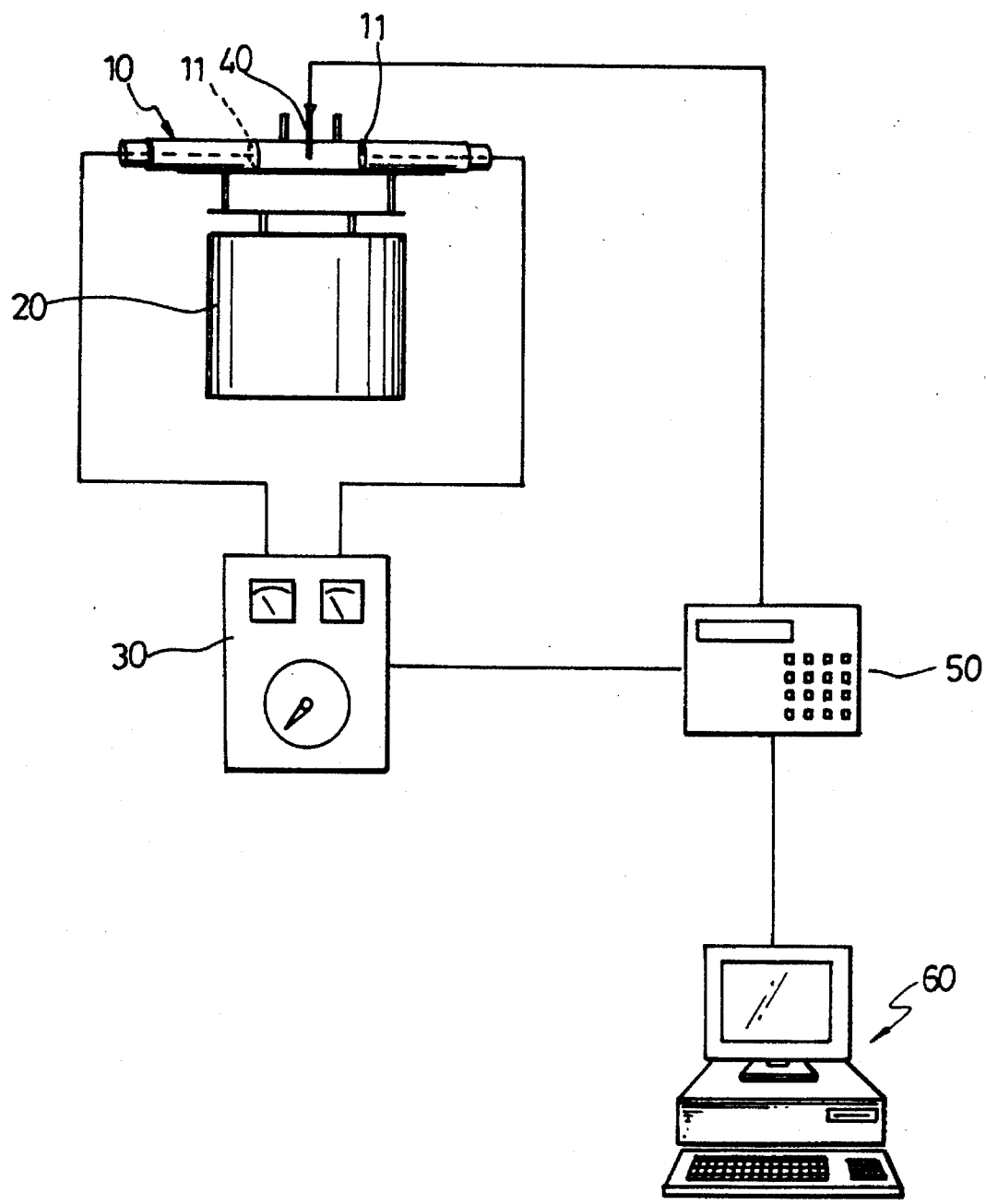
FIG. 1 shows the hardware arrangement of the starch gelatinization measuring system of the preferred embodiment of the present invention.

Referring to FIG. 1, a starch gelatinization measuring system in accordance with the present invention is generally comprised of an ohmic heater 10, a shaker 20, a power supply unit 30, a temperature detector 40, a data logger 50, and a computer 60. During the operation, the ohmic heater 10 is mounted on the shaker 20 to hold sample starch, and shaker 20 is operated to shake the ohmic heater 10 and sample starch. The power supply unit 30 is connected to a pair of plate electrodes 11 in the ohmic heater 10. During the measurement, sample starch is heated to 100° C. by 30–120 voltage. The temperature detector 40 is put in sample starch to detect its temperature. The data logger 50 records the temperature, electric current, voltage, and then sends the recorded data to the computer 60 for analysis.

Figure 2:
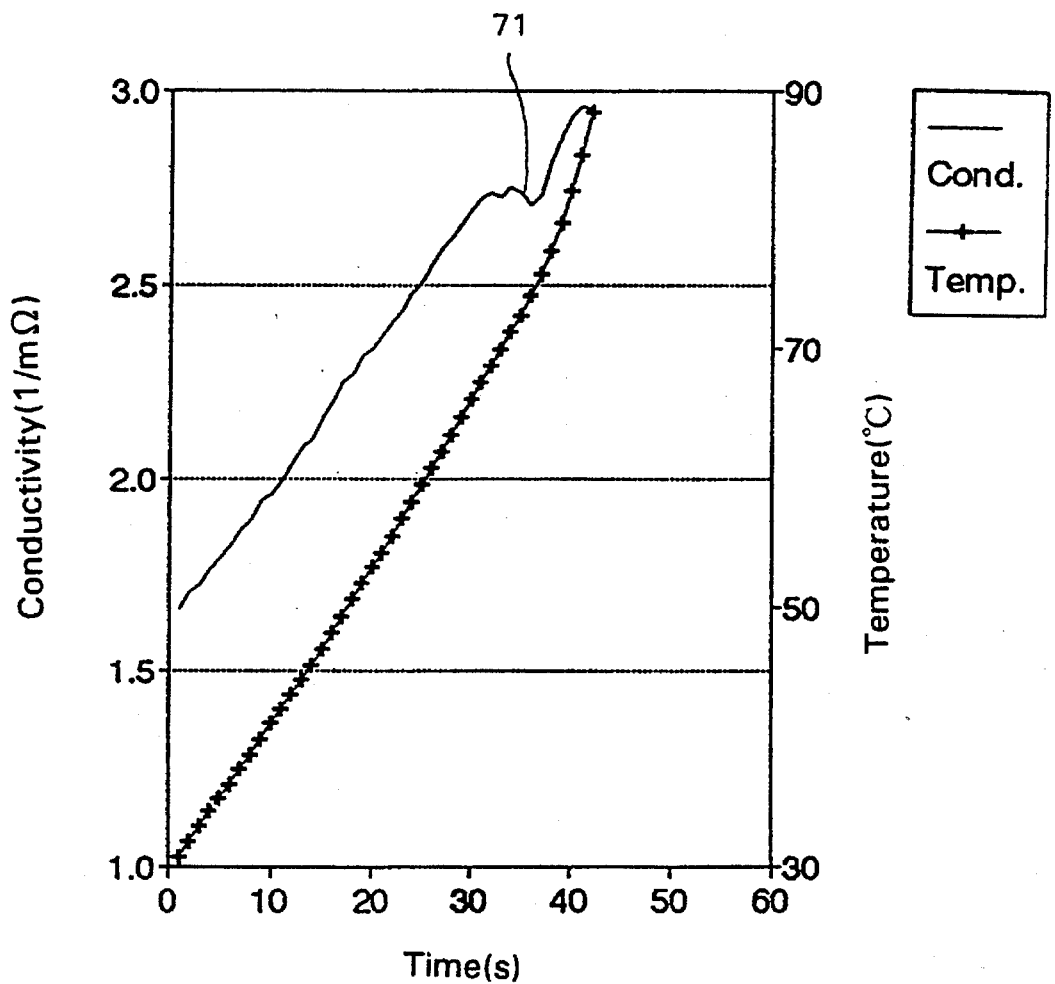
FIG. 2 is a conductivity curve obtained from potato starch during its gelatinization according to the present invention.

FIG. 2 shows a conductivity curve obtained from potato starch during its gelatinization. During the measurement, AC 30–120 V is employed to the ohmic heater, and the measuring time can be reduced when high voltage is used. The conductivity curve of FIG. 2 is obtained by employing AC 100 V to the ohmic heater, and the measurement was finished within 1 minute. However, when relatively lower AC voltage is employed, the resolution of the conductivity curve is relatively increased, and the accuracy of the measurement is relatively improved. During starch gelatinization, a peak curve 71 occurs. The degree of starch gelatinization is calculated by utilizing the electrical conductivity change like this peak curve 71. The calculation of the conductivity and the degree of starch gelatinization is outlined hereinafter.

CALCULATION OF CONDUCTIVITY:

$$\sigma = L/AR$$

in which:

σ: conductivity

L: distance between the plate electrodes of the ohmic heater

A: cross section of the ohmic heater

R: resistance

CALCULATION OF THE DEGREE OF STARCH GELATINIZATION:

(1) Starch gelatinization reference value $PA_0$:

Mix non-gelatinization starch sample (the same source of the gelatinized starch sample, whose degree of starch gelatinization is 0%) with distilled water into a suspension, and then measure the conductivity of the suspension so as to obtain a conductivity curve similar to that shown in FIG. 2. Integrate the peak curve so as to obtain the total area of the peaks, and the total area of the peaks is utilized as starch gelatinization reference value $PA_0$.

(2) Starch gelatinization supplement value $PA_1$:

Measure the gelatinized starch sample so as to obtain its conductivity curve, then integrate the peak curve so as to obtain the total area of the peaks. The total area of the peaks is utilized as $PA_1$.

(3) Equation of the calculation of the degree of starch gelatinization:

The degree of gelatinization of the starch sample under test can be obtained by means of comparing its starch gelatinization supplement value $PA_1$ with the reference value $PA_0$. The formula for the degree of starch gelatinization is as follows: Degree of starch gelatinization $$(\%SG)=(1-(PA_1/PA_0))\times 100 \qquad (I)$$

Figure 3:
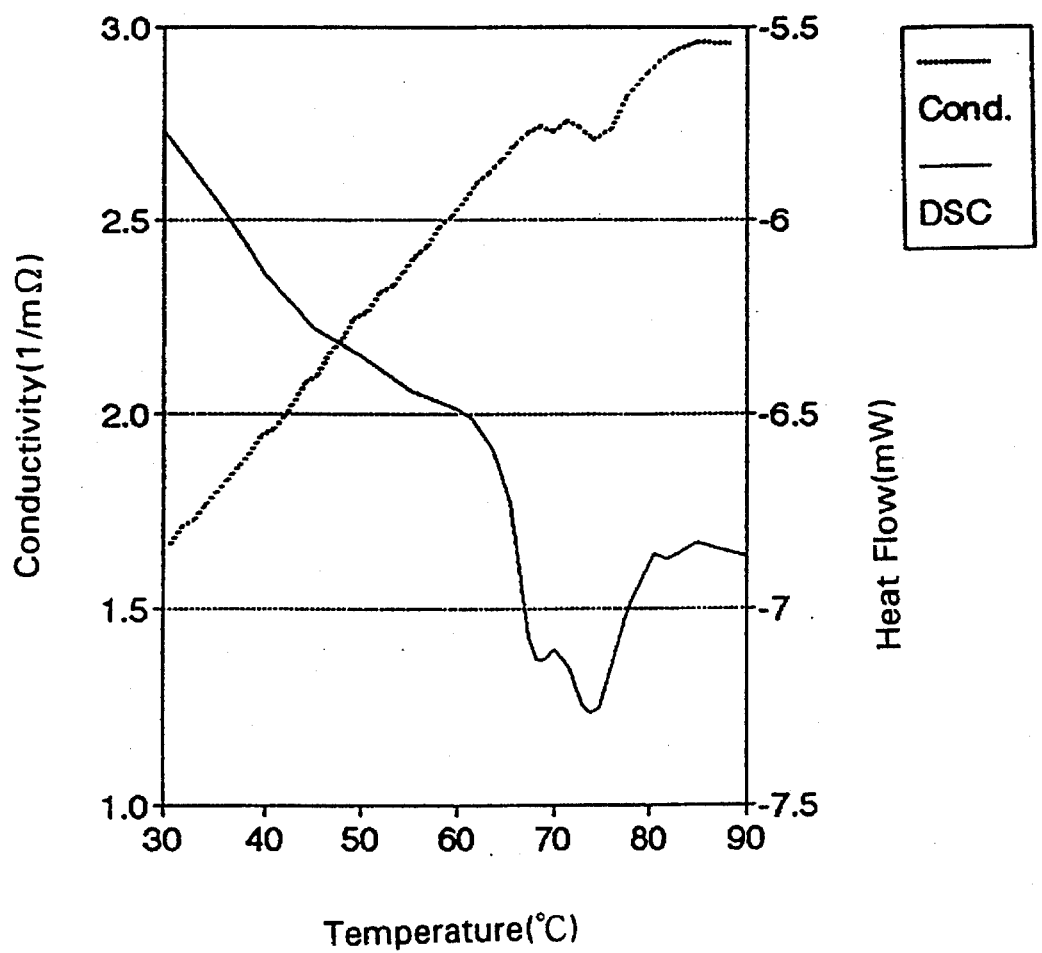
FIG. 3 is a comparison chart showing a conductivity curve and a thermal-flux curve respectively measured from same starch by the starch gelatinization measuring system of the present invention and DSC (differential scanning calorimetry).

Referring to FIG. 3, when comparing the thermal flux curve obtained subject to DSC with the conductivity curve obtained subject to the present invention, we can find that both curves have a similar peak shape at the same horizontal coordinate (temperature) location. Therefore, the measuring system of the present invention accurately indicates the starch gelatinization in which the conductivity of the starch sample drops when starch gelatinization occurred, due to the swelling of starch granules. After gelatinization, the conductivity of the starch sample increases since the electrical conductivity is proportional to temperature.

The measuring system of the present invention is practical for measuring the degree of starch gelatinization by means of sampling measurement or on-line measurement. When the measuring system of the present invention is employed for on-line measurement, the measuring result can be immediately fed back to the main control unit of the production line to automatically adjust the control parameters so that the quality of the product can be maintained at the desired level. To use the measuring system in the production line, the ohmic heater, the temperature detector, and the electrodes could be installed on the production line, and the starch gelatinization data can then be automatically monitored on-line and bed back to the main control unit of the production line. For example, in a liquid food sterilization production line in which the food contains starch, the starch of the liquid food will be gelatinized when heating. When the starch of the liquid food is gelatinized, it becomes thick, and the flowing speed will be relatively slowed down. If the flowing speed of the liquid food is slowed down, it may be overheated. When the starch of the liquid food is gelatinized, it is immediately detected by the measuring system of the present invention, and the information can be immediately fed back to the main control unit, causing it to relatively accelerate the delivering speed of the liquid food.

EXAMPLE I

To measure the degree of starch gelatinization of a partially gelatinized potato starch sample, the reference value of the non-gelatinization potato starch of the same lot is first measured as $PA_0=0.51$. The starch gelatinization supplement value of the partially gelatinized potato starch sample is measured as $PA_1=0.23$. Thus, the degree of starch gelatinization of sample: $(\%SG)=(1-0.23/0.51)\times 100=54.9\%$. The degree of starch gelatinization of the same sample is 55% when tested by DSC. Therefore, both methods shows an approximately equal result.

EXAMPLE II

To measure the degree of starch gelatinization of a partially gelatinized corn starch sample, the reference value of the non-gelatinization corn starch of the same lot is measured as $PA_0=0.56$. The starch gelatinization supplement value of the partially gelatinized corn starch sample is measured as $PA_1=0.14$. Thus, the degree of starch gelatinization of sample: $(\%SG)=(1-0.14/0.56)\times 100=75.0\%$. The degree of starch gelatinization of the same sample is 75% when tested by DSC. Therefore, both methods shows an approximately equal result.

It is to be understood that the drawings are designed for purposes of illustration only, and are not intended as a definition or limits of the scope and spirit of the invention disclosed.

What the invention claimed is:

1. A starch gelatinization measuring system comprising:
    an ohmic heater to hold and to heat the starch sample to be measured, said ohmic heater having a pair of plate electrodes for heating;
    a power supply unit electrically connected to said ohmic heater to control the supply of electric current and electric voltage to the plate electrodes of said ohmic heater;
    a temperature detector controlled to detect the temperature of the starch sample being heated by said ohmic heater;
    a data logger electrically connected to said power supply unit and said temperature detector to record the data of temperature, electric current, electric voltage during heating; and
    a computer electrically connected to said data logger to analyze the data provided by said data logger.

2. The starch gelatinization measuring system of claim 1 wherein said temperature detector is a thermometer.

3. The starch gelatinization measuring system of claim 1 wherein said starch sample is a foodstuff sample containing starch.

4. The starch gelatinization measuring system of claim 1 wherein said starch sample is a chemical product sample containing starch.

5. The starch gelatinization measuring system of claim 1 wherein said ohmic heater is mounted on a shaker.

* * * * *